United States Patent [19]

Koermer et al.

[11] Patent Number: 4,701,527
[45] Date of Patent: Oct. 20, 1987

[54] SYNTHESIS OF SALICYLAMIDES WITH IMPROVED REACTION KINETICS AND IMPROVED EFFECTIVE YIELDS

[75] Inventors: Gerald S. Koermer, Springfield; Eddie N. Gutierrez, Fort Lee; Maryfrances Prorok, Tenafly, all of N.J.

[73] Assignee: Lever Brothers Company, New York, N.Y.

[21] Appl. No.: 673,308

[22] Filed: Nov. 20, 1984

Related U.S. Application Data

[63] Continuation-in-part of Ser. No. 558,066, Dec. 5, 1983, abandoned.

[51] Int. Cl.$^4$ ............................................. C07C 103/22
[52] U.S. Cl. ..................................... 544/277; 548/179; 548/163; 548/195; 549/474; 549/480; 549/481; 564/134; 564/139; 564/169; 564/179
[58] Field of Search ............... 564/134, 139, 169, 179; 544/277; 548/179, 195, 163; 549/480, 474, 481

[56] References Cited

U.S. PATENT DOCUMENTS

| | | | |
|---|---|---|---|
| 2,773,096 | 12/1956 | Sahyun | 564/134 |
| 3,244,520 | 4/1966 | Schulte | 564/134 |
| 3,907,893 | 10/1979 | Parker | 260/562 R |
| 4,201,715 | 11/1980 | Deinhammer | 546/316 |
| 4,287,191 | 9/1981 | Coburn | 564/169 |
| 4,358,443 | 11/1982 | Coburn | 564/169 |

FOREIGN PATENT DOCUMENTS

| | | | |
|---|---|---|---|
| 0590180 | 1/1960 | Canada | 564/179 |
| 56571 | 1/1960 | United Kingdom | 564/134 |

OTHER PUBLICATIONS

Thakur, Chemical Abstracts 81: 135769a.
March, "Advanced Organic Chemistry", 2nd Ed., pp. 386–387, McGraw-Hill (1977).
"The Chemistry of Imines", by Robert Q. Layer, pp. 489–510, Chemical Reviews, 63, (1963).
Advanced Organic Chemistry, Second Edition, by Jerry March, p. 806, McGraw-Hill Book Co., 1977.
J. VanAllan and C. F. H. Allen, "Organic Syntheses Collective Volume 3", pp. 765–767 (1946).
VanAllan, J. A., "Journal of the American Chemical Society", 69, 2913 (1947).
Kirby, A. J. et al., "Journal of the Chemical Society", Perkin Transactions II (1979), p. 1610.
Fife, T. H. et al., "Journal of the American Chemical Society", 105 74 (1983).
Menger, F. and Smith, J. H. J. Amer. Chem. Soc., 91, 5346 (1969).
Satchell, D. P. and Secemski, I., J. Chem. Soc., B, 130 (1969).
Khan, M. N., J. Org. Chem., 48, 2046 (1983).

Primary Examiner—David M. Naff
Assistant Examiner—Robert Benson
Attorney, Agent, or Firm—Gerard J. McGowan, Jr.; James J. Farrell

[57] ABSTRACT

A method of synthesizing with improved reaction kinetics and improved effective yields salicylamide compounds of the formula:

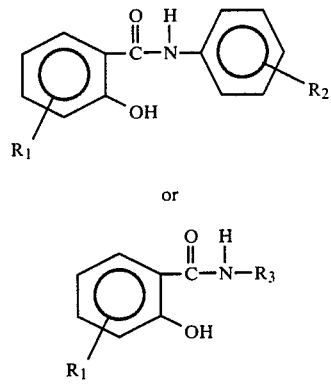

wherein $R_1$ is a substituent selected from the group consisting of —H, —$COC_nH_{2n+1}$ and —$C_nH_{2n+1}$ wherein n is an integer with a value of from 1 through to about 15, $R_2$ is a substituent selected from the group consisting of —H, —CN, —$NO_2$, —F, —Cl, —Br, —I, —$CF_3$, —$CBr_3$, —$CCl_3$, —$CI_3$ and $R_1$ and $R_3$ is an $R_2$ substituted heterocyclic compound selected (e.g.) from the group consisting of furan, thiazole, benzothiazole and purine which comprises reacting a phenyl salicylate ester bearing an $R_1$ substituent on the benzene ring of the salicylic acid portion thereof with an $R_2$ substituted aniline or a heterocyclic amine $NH_2$—$R_3$ and with a Lowry-Bronsted acid catalyst, optionally in the presence of an inert solvent such as a halogenated or unhalogenated aromatic compound or a polyethylene glycol of average molecular weight 1000 to 6000 or mixtures thereof at a temperature of above about 150° C. for about one half to about 4 hours. When the Lowry-Bronsted acid catalyst takes the form of the hydrochloride salt of the reactant aniline or heterocyclic amine the amount of the free reactant aniline or heterocyclic amine is reduced proportionately.

21 Claims, No Drawings

SYNTHESIS OF SALICYLAMIDES WITH IMPROVED REACTION KINETICS AND IMPROVED EFFECTIVE YIELDS

This is a continuation-in-part of application Ser. No. 558,066, filed Dec. 5, 1983, now abandoned.

This invention relates to a new and improved process for the preparation of substituted salicylamides with improved reaction kinetics and effective yields from substituted phenyl salicylates and substituted anilines or heterocyclic amines.

Salicylamide compounds, especially those bearing n-alkyl or n-alkanoyl substituents in the benzene ring of the salicylic acid portion thereof have numerous uses. U.S. Pat. Nos. 4,358,443 and 4,287,191 teach the use of such compounds as bactericides and as anti-dental plaque agents. Commonly assigned U.S. Pat. No. 4,560,549 (hereinafter referred to as Ritchey) issued on Dec. 24, 1985 teaches the use of a wide variety of salicylamide compounds as (inter alia) anti-inflammatory and analgesic agents. The disclosure of Ritchey is hereby incorporated by reference in its entirety.

Commonly assigned U.S. patent application Ser. No. 555,760, abandoned in favor of continuation-in-part application Ser. No. 673,307, filed Nov. 20, 1984, U.S. Pat. No. 4,659,826 (hereinafter referred to as Schwarz) discloses an uncatalyzed process for the preparation of substituted salicylamides from substituted phenyl salicylate esters and substituted anilines or heterocyclic amines. The disclosure of Schwarz is also hereby incorporated by reference in its entirety.

The invention particularly pertains to a new and improved process for the speedy and efficient synthesis of substituted salicylamides wherein a substituted phenyl salicylate is reacted with an excess quantity of a substituted aniline or a substituted heterocyclic amine together with a Lowry-Bronsted acid catalyst in a neat melt or in the presence of a diluent which does not interfere with the formation of the substituted salicylamide products. Thereafter, any standard purification procedure or the one disclosed by Schwarz enables the recovery of the substituted salicylamide product in greatly enhanced yields and purity.

The synthesis of a typical unsubstituted salicylamide is conventionally conducted by the reaction of salicylic acid and aniline in the presence of phosphorus trichloride as a condensing agent. U.S. Pat. Nos. 2,763,683; 3,221,051; 3,221,052; and 3,231,611 describe various processes for the preparation and purification of salicylanilide. However, while the processes described therein are presumably quite effective for the preparation and purification of the parent salicylanilide, they are not practical for the preparation of salicylanilides substituted in the salicyl and/or aniline portions of the molecule or other salicylamide compounds wherein the aniline portion of the molecule is wholly replaced by a substituted or unsubstituted heterocyclic amine.

Ritchey describes the synthesis of salicylamide compounds by the reaction of 5-acyl or 5-alkyl salicylic acid with a substituted aniline in a reaction solvent such as chlorobenzene on the presence of phosphorus trichloride adopting the teachings of U.S. Pat. No. 4,287,191 in that regard.

There is another somewhat more cumbersome method for the preparation of salicylamides known as the salol reaction. Salol is a common name for phenyl salicylate and the salol process involves the formation of amides of salicylic acid by the heating of phenyl salicylate with an amine which may be an aniline or a heterocylic amine. The earliest report relative to the salol process appears to be by M. Schopff, Ber. 25, 2740 (1892). A concise description of the salol process in the English language is contained in the Merick Index, 8th Edition, page 1211 together with a listing of various other publications in which the salol reaction has been mentioned or discussed.

According to the salol process, a given quantity of phenyl salicylate is heated with at least a stoichiometric corresponding quantity of aniline, usually in a high boiling aromatic diluent at temperatures approaching and even exceeding 200° C. for several hours. The resulting reaction product is thereafter allowed to crystallize, washed with ligroin and optionally recrystallized from ethanol. The aforementioned process has been described with reference to the preparation of both the parent salicylanilide as well as several salicylanilides where the substitution has been in the benzene ring of the aniline portion alone.

According to a report by C. F. H. Allen, et al. in "Organic Synthesis, Collective Volume III", 765 (1955), when the parent salicylanilide compound is synthesized the yield is only about 70% and moreover, the resulting product has a persistent pink color which is not easily removed. While Allen, et al. do report higher yields in the syntheses of the other salicylamides, it is interesting to note that the only vaiation from the basic salol process synthesis of salicylanilide suggested therein a one involving the use of different anilines and hetercyclic amines. There is no suggestion made therein with respect to the utility or otherwise of the salol process in those cases where the phenyl salicylate reactant itself incorporates a substituent or substituents upon its salicylic acid benzene ring.

Due consideration of mechanistic concepts enables one to conclude that substitution of the benzene ring of the salicylic acid portion of the phenyl salicylate molecule with an alkyl and especially an alkanoyl group would lead to considerable more complexity in the reaction pathway as a result of the complexation of the aniline or other amine with the alkyl or alkanoyl substituent group. The result would be low yields of the desired product, increased side reactions and more difficulty in purifying the desired salicylamide product.

According to the process disclosed by Schwarz, a pure substituted phenyl salicylate (e.g., 5-octanoyl phenyl salicylate) and a pure substituted aniline (e.g., 3-amino benzotrifluoride) are reacted in a neat melt or in the presence of a diluent. As the reaction proceeds and the reactants are consumed, the reaction rate slows considerably. After 4 hours reaction time 70–80% conversion of the starting phenyl ester is realized and the rate of further reaction is very low. In fact, Schwarz reports reaction times as long as 6 hours. Thus for practical reaction times the reaction yield is limited to 70–80%.

It has now been surprisingly discovered that the presence of Bronsted acid catalysts in the reaction mixture of Schwarz accelerates the reaction rate and improves the yield significantly so that essentially complete (94–100%) conversion of the starting reactants occurs in 2.5 to 3.5 hours. As a result increased efficiency in raw material use, somewhat shorter reaction times and easier isolation and purification of the product salicylamide is made possible.

In terms of prior art, the effect of said additives on amidation is controversial. For example in the amidation of unsubstituted phenyl salicylate, (a convenient analog) evidence is contradictory. Menger, F. Smith, J. H., J. Amer. Chem. Soc., 91, 5346 (1969) indicate that n-butylamine hydrochloride retards the rate of aminolysis by 20%. Satchell, D. P. and Secemski, I., J. Chem. Soc., B, 130 (1969) find acid gives no acceleration in acetonitrile but 64–88% increase in ether. Thus the effect of acids in the Schwarz reaction scheme would be difficult to predict, see, e.g., Khan, M. N., J. Org. Chem., 48, 2046 (1983). Alternatively, U. S. Pat. No. 4,201,715 teaches the anilidization of carboxylic acid esters using equimolar amounts of magnesium dianilide or aluminum trianilide. This method uses stoichiometric quantities of expensive reagents and results in waste disposal problems. In addition, these reagents may not be compatible with phenolic hydroxyl groups present in salicylic esters.

The Lowry-Bronsted acid catalyst must be strong enough to be substantially ionized and may be from a variety of sources such as aliphatic or aromatic carboxylic acids or a mineral acid such as hydrogen halides, sulfuric acid, phosphoric acid, etc. It is also particularly convenient to utilize the hydrochloride or other hydrogen halide salt of an $R_2$ substituted anilines (See definition of $R_2$ given below) as such a catalyst. In its most convenient aspect, the hydrochloride salt of the reactant aniline or heterocyclic amine is used.

This is convenient not only for ease of handling but also because excess aniline or heterocyclic amine reactant is normally removed as the hydrochloride salt during the work-up and isolation of the product salicylamide in accordance with the procedure suggested by Schwarz. Thus another source of impurities is not introduced.

Accordingly, this invention relates to a new process with improved reaction kinetics and improved effective yields for the preparation of salicylamides of the type

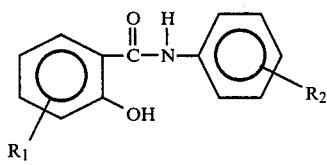

wherein $R_1 =$ —H, —$COC_nH_{2n+1}$ or —$C_nH_{2n+1}$, wherein n is an integer with a value of from 1 through to about 15 and $R_2 =$ H, —CN, —$NO_2$, —F, —Cl, —Br, —I, —$CF_3$, —$CBr_3$, —$CCl_3$, —$CI_3$ and (other groups) from substituted or unsubstituted phenyl salicylates and substituted or unsubstituted anilines. $R_2$ will generally be an electron withdrawing group although it may also be electron donating in which case it may, optionally, be identical with $R_1$. The term "anilines" as used herein is intended to embrace aromatic amines in general, whether they are heterocyclic or not.

Moreover, in another embodiment of this invention, the inventive process relates to the preparation with improved reaction kinetics and improved effective yields of a salicylamide of the formula shown below:

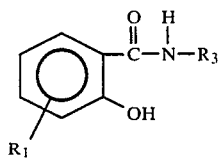

wherein $R_1$ has the meaning already ascribed to it above and $R_3$ is a monocyclic, polycyclic, or heterocyclic aromatic group with or without the same substituents as those represented by $R_2$. Non-limiting examples of heterocyclic amines which are suitable for the practice of this invention include 2-aminofuran, 2-aminothiazole, 2-aminobenzothiazole and 8-aminopurine.

As will be readily apparent to persons of ordinary skill in the art to which the invention pertains, the aromatic amine reactants employed within the practice of the invention (whether or not they are heterocyclic) may be primary or secondary. When the reactant amine is primary, the resulting product will be a secondary salicylamide. When the reactant amine is secondary, the resulting product will be a tertiary salicylamide.

As will also be readily apparent to a person of ordinary skill in the art to which the invention pertains, any of the large number of salicylamide compounds disclosed by Ritchey may be synthesized pursuant to the procedure disclosed and claimed herein provided only that the substituents taught by Ritchey (whether they be upon the salicylic acid benzene ring or upon the aniline or heterocyclic amine ring of the respective salicylamide compounds) do not interfere with the overall reaction scheme of this invention. Again, a person of ordinary skill in the art to which the invention pertains will be able to determine with routine noninventive experimentation which one of the substituents disclosed by Ritchey will or will not interfere with the reaction scheme of the present invention.

According to this invention, a method is provided for the synthesis with improved reaction kinetics and improved effective yields of salicylamide compounds which comprises reacting together about one mole part of a phenyl salicylate ester bearing an $R_1$ substituent on the benzene ring of the salicylic acid portion thereof with about one to 2 mole parts of an $R_1$ or $R_2$ substituted aniline or a heterocyclic amine $NH_2$—$R_3$ in a mole ratio of the aniline or amine to ester of about 1 to 1 to 1.5 to 1 or more preferably about 1.2 to 1 to 1.3 to 1 and in the presence of about 0.01 to about 0.25 and preferably 0.05 to 0.10 mole part of a Lowry-Bronsted acid catalyst. The mole ratio of the aniline or amine to ester selected is based mainly on economics. The most expensive reactant is the salicylate ester and, accordingly, it is desired to use a sufficient excess of the amine or aniline reactant to react completely with the ester. When $R_1$ is —$COC_nH_{2n+1}$, however, large excesses of the amine reactant are undesirable because of Schiff base side product formation by reaction of the amine with the carbonyl group of the side chain. The discovery of this side product formation led to refluxing the acidified reaction mixture in order to hydrolyze any Schiff base present and thereby recover additional desired product. The reaction may optionally be performed in the presence of an inert solvent system such as halogenated or unhalogenated aromatic compounds or a Carbowax (trademark of Union Carbide Corporation) solvent, specifically, a polyethylene glycol of average molecular weight about 1000 to about 6000 or mixtures thereof all having a melting point of up to 120° C. The reaction is performed at a temperature of between about 150° C. to about 225° C., preferably at about 180° C. for about one half to about 4 hours.

When the Lowry-Bronsted acid catalyst takes the form of the hydrochloride salt of the reactant aniline or heterocyclic amine the amount of the free reactant aniline or heterocyclic amine is reduced proportionately.

Thereafter, the product salicylamide compound is recovered using (e.g.) the method suggested by Schwarz. According to Schwarz, the reaction mixture is dissolved in a polar organic solvent (e.g., ethanol), acidified with a Lowry-Bronsted acid (e.g. hydrochloric acid) and refluxed. The product salicylamide compound is precipitated from the reflux mixture by the addition of water. The precipitated product salicylamide compound is thereafter recovered using any standard separation technique, e.g. filtration.

The polar organic solvent has a boiling point up to about 200° C. and may be an alkanol, halogenated hydrocarbon or a mixture of these. The reflux step is done at a sufficiently high temperature and for a sufficient time to form the product. The temperature can vary widely depending on the solvent used, e.g. methanol, ethanol, isopropanol, n-propanol and the like. When ethanol is used, the mixture refluxes at about 80° C. It is possible to use temperatures between about 40° C. and 120° C. or even higher if the reflux were operated under pressure. The time of reflux may vary from a few minutes up to an hour or even longer but too lengthy a reflux could result in undesirable hydrolysis of the product. Preferably, reflux will be from about 15 to 30 minutes to minimize undesirable hydrolysis. The lower the temperature the longer the reflux heating time required while higher temperatures require shorter heating times compared to the fifteen minutes preferably used when the temperature is 80° C.

Finally, the product salicylamide compound may, if desired, be purified by recrystallization from (e.g.) ethanol or a ethanol/water mixture. Any other solvent in which the product salicylamide dissolves may be gainfully employed for the foregoing purpose. The choice of a suitable solvent will be a matter of obvious alternatives to a person of ordinary skill in the art to which the invention relates.

The following Examples which are submitted for illustrative purposes only demonstrate the particular utility of the present invention in synthesizing a representative salicylamide compound, i.e., 3'-trifluoromethyl-5-octanoylsalicylanilide with remarkably high reaction rates and improved effective yields.

EXAMPLE 1

5-octanoyl phenyl salicylate is purified by repeated recrystallization from ethanol to a constant melting point, 73°-74° C. No impurities therein are observed in nuclear magnetic resonance (NMR) or infrared (IR) spectra. The purified ester (one mole) is placed in a flask with a mechanical stirrer, thermometer, condenser, rubber septum for withdrawing samples and a nitrogen purge or blanket. After 3-aminobenzotrifluoride (1.2 moles) is introduced into the flask, the resulting reaction mixture is heated to 180° C. The progress of the reaction is followed by periodically withdrawing samples which are analyzed by nuclear magnetic resonance spectroscopy. The product yields are calculated from the relative amount of the reactant ester and the product salicylamide.

In the above, uncatalyzed reaction involving 3-aminobenzotrifluoride and recrystallized 5-octanoyl phenyl salicylate (as reactants) to produce 5-octanoyl 3'-trifluoromethyl salicylanilide (OTS) the following reaction profile is observed:

| Time (Min.) | % Yield OTS |
|---|---|
| 5 | 12 |
| 30 | 27 |
| 60 | 36 |
| 90 | 48 |
| 125 | 61 |
| 160 | 65 |
| 200 | 69 |
| 235 | 71 |

Reaction times exceeding 235 min. do not result in significantly greater yields, since the yield levels off after 200 min. as shown above.

In the instant, and in the succeeding Examples, 0 min. represents the time at which the reaction mixture reaches the temperature of 180° C.

EXAMPLE 2

To the standard reaction mixture of Example 1 is added 10 mole % octanoic acid (based on the reactant ester). The progress of the reaction is as shown below in two separate runs:

| Time (min.) | % Yield (OTS) |
|---|---|
| RUN 1 | |
| 0 | 17 |
| 28 | 57 |
| 64 | 76 |
| 121 | 89 |
| 176 | 100 |
| RUN 2 | |
| 0 | 24 |
| 33 | 57 |
| 60 | 68 |
| 90 | 78 |
| 106 | 79 |
| 165 | 86 |

EXAMPLE 3

To the standard reaction mixture of Example 1 is added 10 mole % 5-octanoyl salicylic acid (based on the reactant ester). The progress of the reaction is as shown below:

| Time (min.) | % Yield (OTS) |
|---|---|
| 0 | 18 |
| 40 | 45 |
| 70 | 63 |
| 120 | 74 |
| 150 | 81 |
| 180 | 83 |
| 235 | 85 |

EXAMPLE 4

The hydrochloride salt of 3-aminobenzotrifluoride is prepared from an equal molar amount of concentrated hydrochloric acid and said aniline and it is used without further purification. An amount equal to 10 % mole % (based on the reactant ester) is added to the reaction mixture of Example 1. The progress of the reaction is as shown below:

| Time (min.) | % Yield (OTS) |
| --- | --- |
| 0 | 20 |
| 32 | 45 |
| 60 | 60 |
| 92 | 68 |
| 121 | 73 |
| 152 | 81 |
| 180 | 100 |

EXAMPLE 5

Synthesis of 3'-Trifluoromethyl-5-Octanoylsalicylanilide Using Phenyl 5-Octanoyl Salicylate Phenyl 5-octanoyl salicylate, 20 g, and 3-amino benzotrifluoride, 12 g, were placed in a 200 ml, 3-necked round bottom flask equipped with a stirrer. Octanoic acid, 0.85 g, corresponding to 10 mole % (based on the salicylate reactant), was added. A nitrogen sparge was introduced and the stirred reaction mixture heated to 185° C. The reaction was monitored via NMR analysis of samples of the reaction mixture with time. After 3 hours at 185° C., conversion of the salicylate was complete. Methanol, 60 ml, was added and the solution was heated to reflux. Next, 3.5 g of 38% hydrochloric acid and 3.5 g of water was added. The acidified solution was refluxed and stirred until a precipitate formed. The reaction mixture, after allowing to stand overnight, was filtered to yield 20 g of crude product. The crude product was purified by trituration with petroleum ether followed by recrystallization from methanol containing 1 g of concentrated hydrochloric acid. The purified product, 3'-trifluoromethyl-5-octanoylsalicylanilide, amounted to 17 g or 71% of theory.

The invention is further defined by and should be read in conjunction with the appended claims.

What is claimed is:

1. A method of synthesizing salicylamide compounds of the formula:

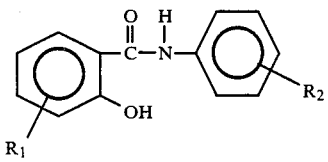

wherein $R_1$ is $-COC_nH_{2n+1}$ wherein n is an integer with a value of from 1 through to about 15 and $R_2$ is a substituent selected from the group consisting of —H, —CN, —NO$_2$, —F, —Cl, —Br, —I, —CF$_3$, —CBr$_3$, —CCl$_3$, —CI$_3$ and $R_1$ which comprises heating a phenyl salicylate ester bearing an $R_1$ substituent on the benzene ring of the salicylic acid portion thereof with an $R_2$ substituted aniline in a mole ratio of said ester to said substituted aniline of about one to one to one to two and with about 0.01 to about 0.25 mole part of a Lowry-Bronsted acid catalyst selected from the group consisting of aliphatic carboxylic acids, aromatic carboxylic acids, hydrogen halides, hydrogen halide salts of $R_2$ substituted anilines and mixtures thereof at a temperature of above about 150° C.

2. The method of claim 1 wherein the phenyl salicylate ester and the aniline are reacted at a temperature in the range of about 150° C. to about 225° C.

3. The method of claim 2 wherein the temperature is about 180° C.

4. The method of claim 1 wherein the Lowry-Bronsted acid catalyst is the hydrochloride salt of the $R_2$ substituted aniline.

5. The method of claim 4 which comprises reacting together about one mole part of the $R_1$ substituted phenyl salicylate ester with about 1.1 mole parts of the $R_2$ substituted aniline and with about 0.1 mole part of the hydrochloride salt of the $R_2$ substituted aniline.

6. The method of claim 1 wherein the Lowry-Bronsted acid catalyst is selected from the group consisting of octanoic acid, 5-octanoyl salicylic acid and 3-aminobenzotrifluoride hydrochloride.

7. The method of claim 1 wherein the quantity of the Lowry-Bronsted acid is about 0.10 mole part.

8. The method of claim 1 wherein the phenyl salicylate ester, the aniline, and the Lowry-Bronsted acid catalyst are reacted for about one half to about four hours.

9. A method of synthesizing salicylamide compounds of the formula:

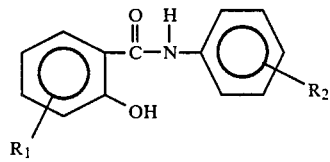

wherein $R_1$ is $-COC_nH_{2n+1}$ wherein n is an integer with a value of from 1 through to about 15 and $R_2$ is a substituent selected from the group consisting of —H, —CN, —NO$_2$, —F, —Cl, —Br, —I, —CF$_3$, —CBr$_3$, —CCl$_3$, —CI$_3$ and $R_1$ which comprises heating a phenyl salicylate ester bearing an $R_1$ substituent on the benzene ring of the salicylic acid portion thereof with an $R_2$ substituted aniline in a mole ratio of said ester to said substituted aniline of about one to one to one to two and with about 0.01 to about 0.25 mole part of a Lowry-Bronsted acid catalyst selected from the group consisting of aliphatic carboxylic acids, aromatic carboxylic acids, hydrochloric acid, hydrochloride salts of $R_2$ substituted anilines and mixtures thereof at a temperature of above about 150° C. in the presence of an organic solvent system selected from the group consisting of halogenated aromatic compounds having a melting point of up to 120° C., unhalogenated aromatic compounds having a melting point of up to 120° C., polyethylene glycols having an average molecular weight of about 1000 to about 6000 and mixtures thereof.

10. A method of synthesizing salicylamide compounds of the formula:

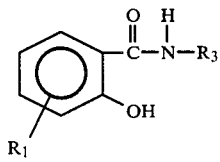

wherein $R_1$ is $-COC_nH_{2n+1}$ wherein n is an integer with a value of from 1 through to about 15 and $R_3$ is an aromatic group, which is carbocyclic or heterocyclic, and is monocyclic or fused on non-fused polycyclic, either unsubstituted or bearing substituents thereon selected from the group consisting of —CN, —NO$_2$, —F, —Cl, —Br, —I, —CF$_3$, —CBr$_3$, —CCl$_3$, —CI$_3$ and R$_1$ which comprises heating a phenyl salicylate ester bearing an R$_1$ substituent on the benzene ring of the salicyclic acid portion thereof with an amine NH$_2$R$_3$ in a mole ratio of said ester to said amine of about one to one to one to two and with about 0.01 to about 0.25 mole part of a Lowry-Bronsted acid catalyst selected from the group consisting of aliphatic carboxylic acids, aromatic carboxylic acids, hydrochloric acid, hydrochloride salts of R$_2$ substituted anilines and mixtures thereof at a temperature of above about 150° C.

11. The method of claim 10 wherein the phenyl salicylate ester and the amine NH$_2$—R$_3$, are reacted at a temperature in the range of about 150° C. to about 225° C.

12. The method of claim 11 wherein the temperature is about 180° C.

13. The method of claim 18 wherein the Lowry-Bronsted acid catalyst is the hydrochloride salt of the heterocyclic amine NH$_2$—R$_3$.

14. The method of claim 13 which comprises reacting together about one mole part of the R$_1$ substituted phenyl salicylate ester with about 1.1 mole parts of the amine NH$_2$—R$_3$ and with about 0.1 mole part of the hydrochloride salt of the amine NH$_2$—R$_3$.

15. The method of claim 10 wherein the Lowry-Bronsted acid catalyst is selected from the group consisting of octanoic acid, 5-octanoyl salicylic acid and 3-aminobenzotrifluoride hydrochloride.

16. The method of claim 10 wherein the quantity of the Lowry-Bronsted acid is about 0.10 mole part.

17. The method of claim 10 wherein the phenyl salicylate ester, the amine NH$_2$—R$_3$ , and the Lowry-Bronsted acid catalyst are reacted for about one half to about four hours.

18. The method of claim 10 wherein R$_3$ is heterocyclic.

19. The method of claim 10 wherein the Bronsted-Lowry acid catalyst is the hydrochloride salt of the amine NH$_2$—R$_3$.

20. A method of synthesizing salicylamide compounds of the formula:

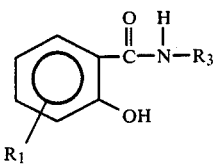

wherein R$_1$ is —COC$_n$H$_{2n+1}$ wherein n is an integer with a value of from 1 through to about 15 and R$_3$ is an aromatic group, which is carbocyclic or heterocyclic, and is monocyclic or fused or non-fused polycyclic, ether unsubstituted or bearing substituents thereon selected from the group consisting of —CN, —NO$_2$, —F, —Cl, —Br, —I, —CF$_3$, —CBr$_3$, —CCl$_3$, —CI$_3$ and R$_1$ which comprises heating a phenyl salicylate ester bearing an R$_1$ substituent on the benzene ring of the salicylic acid portion thereof with an amine NH$_2$R$_3$ in a mole ratio of said ester to said amine of about one to one to one to two and with about 0.01 to about 0.25 mole part of a Lowry-Bronsted acid catalyst selected from the group consisting of aliphatic carboxylic acids, aromatic carboxylic acids, hydrochloric acid, hydrochloride salts of R$_2$ substituted anilines and mixtures thereof at a temperature of above about 150° C. in the presence of an organic solvent system selected from the group consisting of halogenated aromatic compounds having a melting point of up to 120° C., unhalogenated aromatic compounds having a melting point of up to 120° C., polyethylene glycols having an average molecular weight of about 1000 to about 6000 and mixtures thereof.

21. The method of claim 10 wherein the heterocyclic aromatic group R$_3$ is one selected from the group consisting of furan, thiazole, benzothiazole and purine.

* * * * *